United States Patent [19]

Drost et al.

[11] 4,337,576
[45] Jul. 6, 1982

[54] KNIFE WITH RETRACTABLE BLADE

[76] Inventors: Jim L. Drost; Myron K. Gordin, both of P.O. Box 289, Oskaloosa, Iowa 52577

[21] Appl. No.: 204,647

[22] Filed: Nov. 6, 1980

[51] Int. Cl.³ .............................................. B26B 1/08
[52] U.S. Cl. ........................................ 30/162; 30/293
[58] Field of Search ........................ 30/162, 163, 293

[56] References Cited

U.S. PATENT DOCUMENTS

| 3,657,812 | 4/1972 | Lee | 30/162 |
| 3,885,308 | 5/1975 | Gordin | 30/162 |
| 4,209,900 | 7/1980 | Gilbert | 30/162 |

*Primary Examiner*—James M. Meister
*Attorney, Agent, or Firm*—Rudolph L. Lowell; G. Brian Pingel

[57] ABSTRACT

A knife of a pencil type includes a barrel or outer member in which a slidably carried support or inner member is connected in an end-to-end relation with a blade assembly for movement of the blade assembly to extended and retracted positions relative to one end of the barrel member. The blade assembly includes tension fingers that extend from a lower portion of the blade assembly periphery to engage the barrel member and bias such member in an upward direction thereby preventing side-to-side play of the blade assembly in the barrel member and to inhibit upward movement of the blade assembly therein. The blade assembly is also formed with a slight bow to urge the upper portion of the blade assembly against the barrel member and thereby prevent undesired upward movement of the blade assembly when a cutting operation is performed.

7 Claims, 5 Drawing Figures

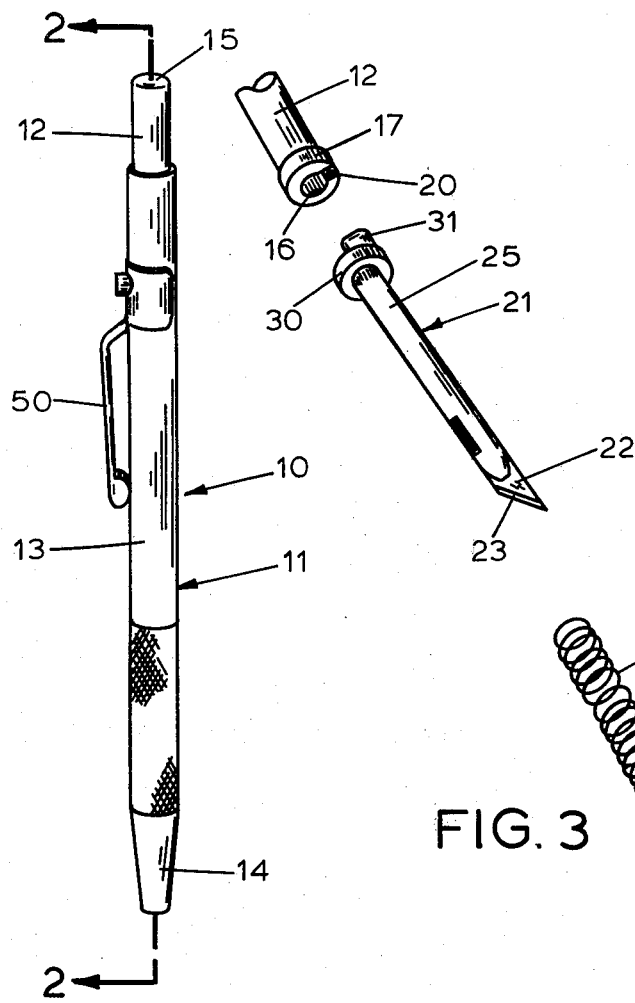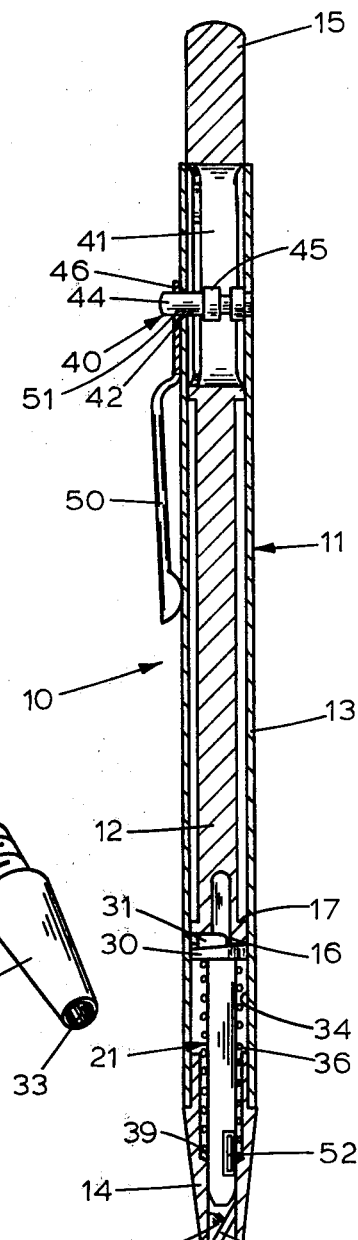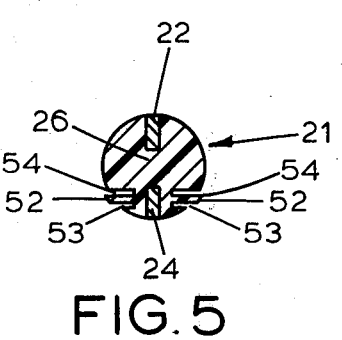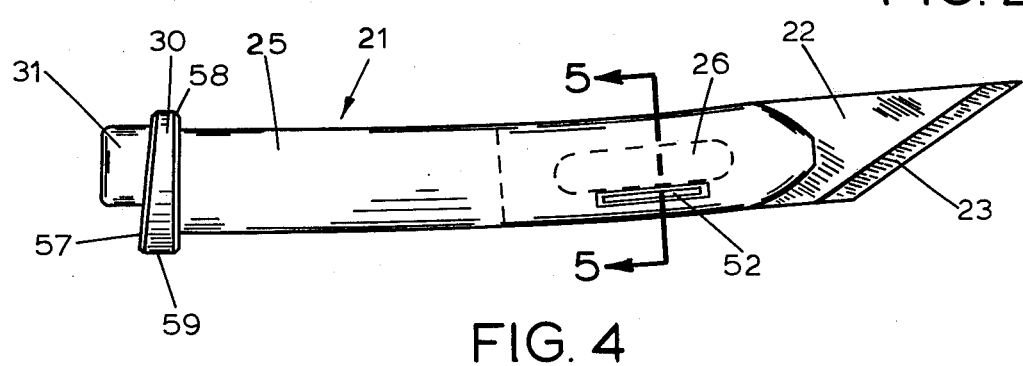

4,337,576

KNIFE WITH RETRACTABLE BLADE

BACKGROUND OF THE INVENTION

1. Field of the Invention

The present invention relates in general to a pencil type knife with a retractable blade and more specifically to such a knife that has means for preventing undesired side-to-side and upward play of the blade during a cutting operation.

2. Description of the Prior Art

Pencil type knives having retractable blades are well-known in the art and are disclosed in U.S. Pat. Nos. 3,885,308 and 3,657,812 issued to Gordon and Lee, respectively. The knives that are disclosed in these patents include a barrel or outer member in which is slidably carried a support or inner member connected in an end-to-end relation with a blade assembly for movement of the blade to extended and retracted positions relative to one end of the barrel member. In an extended position, a portion of the blade assembly projects beyond such one end of the barrel member and support for the blade assembly is provided by the barrel member.

In these prior art devices, it has been economically impractical to form the barrel member and the blade assembly with sufficiently precise tolerances to eliminate substantially all of the side-to-side and up-and-down play of the blade assembly in the barrel member, although it is highly desirable from a user's standpoint, that there be substantially no play in the blade assembly.

The knife of the present invention overcomes this deficiency of the prior art devices by including a blade assembly that is formed to eliminate substantially all side-to-side and upward play in the blade assembly during a cutting operation.

SUMMARY OF THE INVENTION

The present invention provides a knife with a retractable blade and is of a barrel type having a tubular barrel member in which a tubular tool support is located for slidable movement therein between operative and inoperative positions. Releasable latch means coact between the barrel member and the support member to releasably lock the support member in the operative position. A blade assembly located within the barrel member is engaged with one end of the support member for movement therewith between the inoperative position, wherein the blade assembly is retracted inwardly from one end of the barrel member, and the operative position, wherein a portion of the blade assembly extends outwardly from the barrel member one end.

The blade assemby includes tension means for engaging the barrel member to prevent substantially all side-to-side movement of the blade assembly during a cutting operation. Also, the blade assembly has a slight bow to maintain its upper portion in contact engagement with the barrel member thereby preventing undesired upward movement of the blade assembly during a cutting operation.

In a preferred embodiment, the tool support member has a keyway for receiving a key on the blade assembly to prevent rotational movement of the blade assembly and to hold it in a desired cutting alignment whenever extended to the operative position.

BRIEF DESCRIPTION OF THE DRAWINGS

FIG. 1 is a side view in elevation of a preferred embodiment of the knife of the present invention with the blade assembly thereof in a retracted or inoperative position;

FIG. 2 is an enlarged longitudinal sectional view of the knife as seen along the line 2—2 of FIG. 1;

FIG. 3 is an enlarged, exploded, perspective view of a front end member, spring member, blade assembly, and one end of a support member all included as part of the knife of FIG. 1;

FIG. 4 is an enlarged side view in elevation of the blade assembly of FIG. 3; and FIG. 5 is a sectional view taken along the line 5—5 of FIG. 4.

DETAILED DESCRIPTION OF THE INVENTION

Referring to FIG. 1 of the drawings, the present invention provides a knife, shown generally at 10 with a retractable blade. The knife 10 includes a tubular barrel or outer member 11 and an elongated tubular support or inner member 12 which is received in slidable engagement within the barrel member 11 (as shown in FIG. 2). Forming the barrel member 11 is a main body 13 and a conically shaped front end 14 threadably secured to the forward end of the body 13. The support member 12 has a closed rear end section 15 projected outwardly from the rear end of the barrel member 11 and an open front end 16 with a collar 17.

As best seen in FIG. 3, the collar 17 has a notch 20 to serve as a keyway for a blade assembly 21 that abuts against and is engaged with the support member 12. Included in the assembly 21 is a blade 22 having a cutting edge portion 23 and a flange portion 24 (see FIG. 5) about which is molded a generally cylindrically shaped plastic handle portion 25. The blade flange portion 24 is slotted at 26 as indicated in FIGS. 4 and 5 in order that the plastic handle portion 25 extends therethrough for rigid securement to the blade 22.

The rear end of the handle 25 terminates in a collar 30 with a key 31 projecting outwardly therefrom for reception in the keyway 20 to permit abutting engagement between the collars 17 and 30. Together the key 31 and keyway 20 prevent rotation of the blade assembly 21 with respect to the support member 12 thereby insuring that the blade assembly will be maintained in a preferred cutting alignment. The barrel front end 14 has a longitudinally extended bore 33 (FIG. 2) in axial alignment with the body member 12 and is formed with a rear portion 34 of an enlarged diameter relative to its front portion 35. From its rear collar end 30, the blade assembly 21 extends through the bore rear portion 34 for guidable sliding engagement within the front bore portion 35.

A coil spring 36 seated about the blade assembly handle 25 has its respective ends in abutting engagement with the collar 30 and a shoulder 39 formed by the junction of the bore portions 34 and 35. The spring 36 functions to continuously urge the blade assembly 21 toward its retracted or inoperative position shown in FIG. 2 and also holds the rear end of the handle 25 in releasable engagement with the support member 12. It is thus seen that the blade assembly 21 and the support member 12 are axially aligned in an end-to-end relation longitudinally of the barrel member 11 for movement as a unit relative to the barrel member.

Longitudinal movement of the support member 12 in the barrel member 11 to retracted and extended positions of the blade assembly 21 is provided by a latch mechanism 40 (FIG. 2) that is linearly extendible and retractable. The latch mechanism 40 extends transversely of and through a slot 41 in the support member 12 and an opening 42 in the barrel member 11 and is fully shown and described in U.S. Pat. No. 3,657,812 issued Apr. 25, 1972, and incorporated herein by reference. The latch mechanism 40 includes an extendible button or locking member 44 having an enlarged section 45 and an internal coil spring (not shown) that urges the button 44 in an outward direction.

Upon the application of pressure on the closed end 15 of the support member 12 to move the blade assembly 21 into an operative extended position projected forwardly from the barrel front end 14, the button 44 is extended outwardly and the enlarged section 45 moves into an enlarged portion of the slot 41 in the support member 12 to engage and hold the member 12 in its retracted position. A stop plate 46 formed as part of a pocket clip 50 is secured to the outer surface of the barrel member 11 and has an opening 51 that permits the end portion of the button 44 to project therethrough to limit the outward movement of the button 44.

On depressing the button 44 to move the enlarged section 45 out of engagement with the support member 12, the blade assembly 21 is permitted to return to its inoperative position by the action of the spring 36. Thus, movement of the blade assembly 21 from an inoperative position to its operative position and back again is readily accomplished.

As previously described, the keyway 20 (FIG. 3) in the support member collar 17 and the key 31 on the blade assembly handle collar 20 function to prevent rotation of the blade assembly 21 in the barrel 11. The key 31 extends from the upper rear portion of handle 25 and the keyway 20 formed in the circumferential portion of the collar 17 whereby the keyway 20 will receive the key 31 in only one rotational position of the blade assembly 21. Preferably, the keyway 20 and key 31 are arranged so that the cutting edge 23 of the blade 22 is in an imaginary plane extended through the pocket clip 50 and the barrel 11, and faces away from the side of the barrel 11 on which the cip 50 is mounted. In this way, when the knife 10 is used in a cutting operation, it is less likely that the clip 50 will interfere with grasping of the knife by the user.

When the blade assembly 21 is in its operative position, the periphery of the front bore portion 35 of the barrel front end 14 serves as a guide support for the handle portion 25 of assembly 21 to limit side-to-side and up-and-down play or wobble of the blade 22 during a cutting operation. However, it is economically impracticable to have sufficiently precise tolerances in forming the blade assembly 21 and barrel front end 14 so that all such play or wobble is eliminated solely through engagement of the periphery of the bore portion 35 with the periphery of the handle portion 25. Thus, the handle portion 25 is formed with stiff, longitudinally aligned tension fingers 52 positioned near the bottom and on diametrically opposite sides of the handle portion 25 and protrude beyond the periphery thereof.

As shown in FIG. 5, narrow slots 53 and 54, respectively, are formed in the handle portion 25 on opposite sides of the tension fingers 52 to permit a small amount of deflection in the fingers 52. As a result, when the blade assembly 21 is in the barrel front end 14, the deflectable tension fingers 52 engage the periphery of the bore 35 and compensate for any gap that exists between the periphery of such bore and the periphery of the handle portion 25 to thereby prevent side-by-side movement of the blade 22. Also, due to the location of the tension fingers 52 near the bottom of the handle portion 25, the tension fingers 52 provide an upwardly directed biasing pressure on the handle portion 25 to urge the blade assembly 21 against the upper periphery of the bore 35 leaving substantially no clearance therebetween to prevent upward movement of the blade 22 when a cutting operation is performed. Although such biasing does not reduce, and indeed increases, downward play of the blade 22, this is of little, if any, consequence because all normal cutting operations with the knife 10 are performed so that an upward force is exerted on the blade 22 by the material being cut. Additionally, to further prevent upward movement of the blade 22 when a cutting pressure is exerted thereon, the front half of the blade assembly 21 is arcuately formed with a slight upward bow of approximately 3 to 5 degrees. In this way, upward biasing pressure on the handle portion 25 will be sufficient that the handle portion 25 is normally biased against the periphery of the bore 35 leaving no clearance therebetween.

This upward biasing of the blade 22 is further enhanced by the shape of the collar 30 which is formed with an inclined side end surface 57 (best shown in FIG. 4) to provide the collar 30 with a narrow upper portion 58 and a wide portion 59. Thus, when the blade assembly 21 is engaged by the support member 12, only the collar wide portion 59 and key 31 abut against the support member collar 17 to provide an off-center force on the lower portion of the collar 30 maintaining the blade assembly 31 in its extended position. In this way, a torque is exerted on the blade assembly 21 to further urge the upper peripheral portion of the handle portion 25 against the periphery of the bore 35.

Thus, precise and accurate cutting can be performed with the knife 10 through the elimination of substantially all undesired side-to-side and upward movement of the blade 22 during a cutting operation.

I claim:

1. In a knife having a tubular barrel member with a longitudinal bore, a tubular tool support member located within said barrel member bore for slidable movement therein between operative and inoperative positions, releasable latch means coacting between said barrel member and said support member to releasably lock said support member in said operative position, and a blade assembly located within said barrel member bore and engageable with one end of said support member for movement therewith between said inoperative position wherein said blade assembly is retracted inwardly from said one end of said barrel member and an operative position wherein a portion of said blade assembly extends outwardly from said barrel member one end, the improvement wherein said blade assembly comprises:

(a) a blade having a cutting portion at one end and a shank portion at an opposite end,
  (b) a handle in which said shank portion of said blade is rigidly secured, said handle having a generally cylindrically shaped periphery and a pair of diametrically opposed tension means that extend beyond the handle periphery to engage the bore of said barrel member as said blade assembly is moved into said operative position to reduce undesired side-to-side movement of said blade when cutting pressure is exerted thereon.

2. In a knife as recited in clam 1 wherein said blade assembly is arcuately formed with a bowed configuration of at least 3 to 5 degrees to urge the blade assembly against the periphery of the bore of said barrel member to reduce upward movement of said blade when cutting pressure is exerted thereon.

3. In a knife as recited in claim 1, wherein said tool support member and said blade assembly include coacting means to prevent rotation of said blade assembly in said barrel member.

4. In a knife as recited in claim 3 wherein one of said tool support member and said blade assembly has a key at one end and the other has a keyway at an adjacent end to provide said coacting means.

5. In a knife as recited in claim 4 wherein said key and keyway are formed axially off-center of said support member and said blade assembly whereby said key and keyway coact in only one rotational position of said blade assembly.

6. In a knife as recited in claim 1 wherein one of said tool support member and said blade assembly has an inclined end surface that abuts against an end surface of the other to provide an off-center abutment force therebetween to urge the blade assembly against the periphery of the bore of said barrel member to reduce upward movement of said blade when cutting pressure is exerted thereon.

7. In a knife as recited in claim 1 wherein said tension fingers are formed near the bottom of said handle to provide an upwardly directed biasing presure thereon to urge the blade assembly against the bore of said barrel member to reduce upward movement of said blade when cutting pressure is exerted thereon.

* * * * *